(12) United States Patent
Pütter et al.

(10) Patent No.: US 6,315,884 B1
(45) Date of Patent: Nov. 13, 2001

(54) METHOD FOR PRODUCING PHTHALIDES

(75) Inventors: Hermann Pütter, Neustadt; Dieter Baumann, Walldorf; Heinz Hannebaum, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/508,114

(22) PCT Filed: Sep. 5, 1998

(86) PCT No.: PCT/EP98/05626

§ 371 Date: Mar. 20, 2000

§ 102(e) Date: Mar. 20, 2000

(87) PCT Pub. No.: WO99/15514

PCT Pub. Date: Apr. 1, 1999

(51) Int. Cl.$^7$ .......................................................... C25B 3/00
(52) U.S. Cl. ........................ 205/440; 205/441; 205/431; 205/434; 205/435
(58) Field of Search .................................. 205/440, 441, 205/427, 431, 434, 435

(56) References Cited

FOREIGN PATENT DOCUMENTS

| | | | |
|---|---|---|---|
| 2144419-A1 | * | 3/1973 | (DE) . |
| 2510920-A1 | * | 9/1976 | (DE) . |
| WO-97/43464-A | * | 11/1997 | (WO) . |

OTHER PUBLICATIONS

Reference N was cited in the International Search Report.*

* cited by examiner

*Primary Examiner*—Edna Wong
(74) *Attorney, Agent, or Firm*—Oblon, Spivak, McClelland, Maier & Neustadt, P.C.

(57) ABSTRACT

A process for preparing phthalides by

I. reducing phthalic acid or phthalic acid derivatives, where the carboxyl groups may be replaced by units which can be derived from the carboxyl groups by a condensation reaction and where one or more of the hydrogens of the o-phenylene unit may be substituted by inert radicals, at a cathode in a undivided electrolytic cell and dissolved in an electrolyte, II. discharging the electrolyte from the electrolytic cell when the reaction has proceeded to the stage where the molar ratio (M), formed by the proportion of phthalide and the sum of the proportions of phthalide and phthalic acid of phthalic acid derivatives in the electrolyte, is from 0.8:1 to 0.995:1, and III. crystallizing the phthalides from the electrolyte and removing them from the mother liquor, if appropriate after distillative work-up of the electrolyte is described.

12 Claims, No Drawings

METHOD FOR PRODUCING PHTHALIDES

The present invention relates to a novel process for preparing phthalides of particularly high purity by I. reducing phthalic acid or phthalic acid derivatives, where the carboxyl groups may be replaced by units which can be derived from the carboxyl groups by a condensation reaction and where one or more of the hydrogens of the o-phenylene unit may be substituted by inert radicals, at a cathode in an undivided electrolytic cell and dissolved in an electrolyte, II. discharging the electrolyte from the electrolytic cell when the reaction has proceeded to the stage where the molar ratio (M), formed by the proportion of phthalide and the sum of the proportions of phthalide and phthalic acid or phthalic acid derivatives in the electrolyte, is from 0.8:1 to 0.995:1, and III. crystallizing the phthalides from the electrolyte and removing them from the mother liquor, if appropriate after distillative work-up of the electrolyte.

Phthalides are required in particular as intermediates for the synthesis of crop protection agents.

DE A-2 144 419 discloses an electrochemical process for preparing phthalides by cathodic reduction of ammonium phthalamate in an aqueous solution containing up to 50% of organic solvent at temperatures of up to 65° C. on metals having a hydrogen overpotential greater than Cu, for example lead. Under these conditions, the preparation of phthalides is achieved in satisfactory yields if the reduction is carried out in divided electrolytic cells.

The preparation of particularly pure phthalides is described in DE-A-2 510 920. This publication teaches the cathodic reduction of ammoniacal, aqueous solutions of phthalic acid or of phthalic anhydride at temperatures of up to 100° C. on metals having a hydrogen overpotential greater than Cu. Again, the process requires the use of divided electrolytic cells. The phthalide is separated off from the electrolytic mixture by acidifying at from 35 to 100° C., if necessary after removal of excess ammonia, and separating off the precipitated phthalide.

The processes described, however, have the disadvantage of the high expenditure on equipment involved with the use of divided electrolytic cells, since 2 cell circuits are required in this case. In addition, working with 2 cell circuits has the following further disadvantages:

The cell circuits have to be separated by a membrane or a diaphragm; this means an energy loss owing to heat of resistance. Usually, in order to minimize this loss, at least one chamber is charged with an aqueous (>80% $H_2O$) solution of supporting electrolytes. In cathodic reductions, this is the anolyte. This considerably reduces the available options for exploiting the anodic reaction. Normally, the sole anodic product formed is oyxgen.

The preparation of phthalides by electrochemical reduction of phthalic acid derivatives in an undivided electrolytic cell is proposed in the non-prior-published DE Patent Application of the reference No. 19618854.7. In this publication, it is also proposed to purify the phthalide by recrystallization. Details of up to which conversion the electrolysis of the phthalic acid derivatives is to be carried out before it is ended are not given in this publication, neither is the conversion implicitly disclosed to the person skilled in the art in the Examples.

The phthalides prepared by the abovementioned methods are of relatively high purity which is sufficient for most applications. However, in some cases the phthalides are required in a degree of purity which cannot be achieved at all, or only with high expenditure, by using the prior art methods.

In particular when using dimethyl phthalates and ring-substituted derivatives thereof, the phthalide and its starting material are hardly separable by distillation. In principle, this purification problem can be bypassed by carrying out the electrolysis until virtually the total amount of starting material is converted. To produce a 98% pure quality, for example, the starting material has to be converted to the point where the weight ratio of product to starting material is at least 98:2 and the molar ratio is 0.98 to 1. When using dimethyl phthalate (MW 194), a weight ratio of product to starting material of 99:1 is therefore to be aimed for. However, this solution to the purification problem has the disadvantage that the selectivity of the reaction is strongly reduced and that useless byproducts are formed in considerable amounts.

It is an object of the present invention to provide a method for preparing phthalides in high purity, good yields and by an economical and simple technical process.

We have found that this object is achieved by the process decribed at the outset.

The starting materials used for preparing the phthalides are in particular those of the formula (I)

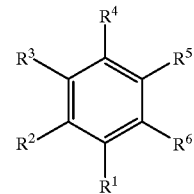

where the substituents have the following meanings:
$R^1, R^2, R^3$ and $R^4$: are each, independently of one another, hydrogen, $C_1$- to $C_4$-alkyl or halogen
$R^5, R^6$:
  a) are each, independently of one another, —COOH or COOX, where X is $C_1$- to $C_4$-alkyl,
  b) one of the substituents $R^5$ or $R^6$ is —COONY$_4$ and the other substituent is CONH$_2$, where Y is $C_1$- to $C_4$-alkyl or hydrogen,
  c) $R^5$ and $R^6$ together are —CO—O—CO—.

Particular preference is given to those derivatives of phthalic acid where $R^1$, $R^2$, $R^3$ and $R^4$ are each hydrogen, and among these in particular to the di($C_1$- to $C_3$-alkyl) phthalates, especially to dimethyl phthalates.

The electrochemical conversion of these starting materials can be carried out for example by the method described in DE-A-19618854.7.

Electrode materials which are suitable for this process (both as cathode and anode) are in particular commercially available electrodes made of graphite or carbon.

The electrolyte is usually a 2 to 40% by weight strength solution of phthalic acid or a phthalic acid derivative in an organic solvent or a mixture of an organic solvent and water, the mixture generally containing less than 50% by weight, preferably less than 25 and particularly preferably less than 5% by weight of water.

Useful organic solvents are in particular aliphatic $C_1$- to $C_4$-alcohols, in particular methanol or ethanol, or mixtures of such alcohols with a carboxamide such as dimethylformamide or t-butylformamide.

Suitable conducting salts contained in the electrolytes are, for example, quaternary ammonium salts, such as tetra($C_1$- to $C_4$-alkyl)ammonium halides or tetra($C_1$- to $C_4$-alkyl) ammonium tetrafluoroborates and preferably methyltributylammonium methylsulfate or methyltriethylammonium methylsulfate, usually in amounts of from 0.4 to 10% by weight, based on the electrolyte.

For the anodic coproduction process, it is advisable to use as anodic depolarizer a conventional organic compound whose suitability for the electrochemical oxidation is generally known to the person skilled in the art. Some of the anodic coproduction processes are preferably carried out in the presence of a mediator. Suitable anodic coproduction processes are described, for example, in D. Kyriakou, Modern Electroorganic Chemistry, Springer, Berlin 1994, Chapter 2.

Useful anodic coproduction processes are in particular the oxidation of C—O or C—N single or double bonds, for example the oxidation of carboxylic acids, or the oxidative C—C coupling in particular of naphthalenes or activated CH groups and the oxidation of methyl groups attached to an aromatic ring to give aldehydes.

The use of methylbenzene or ring-substituted derivatives of methylbenzene where 1 to 3 hydrogens of the phenyl radical may be replaced by $C_1$- to $C_6$-alkyl radicals or $C_1$- to $C_4$-alkoxy radicals has been found to be particularly favorable. Examples of such anodic depolarizers include p-xylene and p-tert-butyltoluene.

When preparing aldehydes as coproducts, the use of the abovementioned alcohols as solvents is recommended, since the aldehydes are acetalized and protected against further oxidation.

The other process parameters such as temperature and current density are not crucial as long as they are kept within the conventional limits for the electrochemical reaction of organic compounds. They are further specified for example in DE-A-2510920.

When the reaction has proceeded to the stage where the molar ratio (M), formed from the proportion of phthalide and the sum of the proportion of phthalide and phthalic acid or phthalic acid derivatives, in the electrolytes is from 0.8:1 to 0.995:1, preferably from 0.83:1 to 0.99:1 and particularly preferably from 0.86:1 to 0.95:1, the electrolyte is discharged from the electrolytic cell.

The reaction can be carried out both batchwise and continuously.

If the process is carried out continuously, it is advantageous to adjust the continuous discharge of the electrolyte and the continuous supplementation of the inert components of the electrolyte and of the solvents and conducting salts and of the starting materials for the electrochemical reaction to each other and to the reaction rate in such a way that the concentration of all components of the electrolyte remains essentially constant. This applies in particular to the molar ratio (M) which should vary only within the defined range.

In general, the discharged electrolyte (hereinbelow referred to as "crude phthalide") is worked up distillatively prior to the crystallization. This is preferably carried out in the following manner:

Firstly the solvent and then a fraction containing the phthalides is distilled off from the electrolyte. The distillation is advantageously carried out by connecting separately, in addition to the solvent and the fraction containing mainly the phthalides, a further fraction containing mainly the coproduct. The remaining distillation residue generally contains mainly the conducting salt.

The distillation of the crude phthalide is generally carried out at a pressure of from 1 to 100 mbar and at from 100 to 220° C. For this purpose, for example a thin-layer evaporator is used. The distillation residue, which in most cases consists essentially of conducting salt, can be recycled into the electrolytic cell.

The crude phthalide, which is, if appropriate, pre-purified in this manner, is subsequently purified by crystallization.

There are no limitations with respect to the crystallization method used. The crystallization can be carried out continuously or batchwise, in one stage or in a plurality of stages.

The crystallization is preferably carried out without addition of an auxiliary, in partiuclar without addition of an organic solvent.

The crystallization is preferably carried out in one stage. In another preferred embodiment of the invention, the crystallization is carried out as a fractional crystallization.

In a fractional crystallization, all stages producing crystals of a purity higher than that of the crude phthalide that is introduced are usually referred to as purification stages and all other stages are referred to as stripping stages. Multistage processes are advantageously operated by the countercurrent principle where in each stage the crystals are separated from the mother liquor after the crystallization, and these crystals are fed into the respective stage having the next highest degree of purity, while the crystallization residue is fed into the respective stage having the next lowest degree of purity.

The temperature of the solution or melt during the crystallization is advantageously from −10 to 75° C., in particular from 20 to 70° C. The solid content in the crystallizer is usually from 0 to 70 g, preferably from 30 to 60 g, per 100 g of material charged.

In a further advantageous embodiment of the invention, the crystallization is carried out in an apparatus where the crystals grow on cooled surfaces in the crystallization apparatus, ie. surfaces which are mounted in the apparatus (for example the layer crystallization process of Sulzer Chemtech (Switzerland) or the static crystallization process of BEFS PROKEM (France)).

The crystallization can furthermore be carried out by cooling the walls of the apparatus or by evaporating a solution of the crude phthalide under reduced pressure. Particularly suitable for this purpose are 5–30% by weight strength solutions of the crude phthalide in methanol, where the methanol may be the methanol which is used as solvent in the electrolyte.

In the crystallization by cooling, the heat is carried off via scrape chillers which are connected to a stirring tank or a vessel without stirrer. The circulation of the crystal suspension is in this cane effected using a pump. Additionally, it is also possible to carry off the heat via the wall of a stirring tank using a close-clearance stirrer. A further preferred embodiment of the crystallization by cooling entails the use of cooled-plate crystallizers as manufactured, for example, by Gouda (The Netherlands). A further suitable variant of the crystallization by cooling comprises carrying off the heat via conventional heat exchangers (preferably steel-and-tube or plate heat exchangers). These apparatuses, in contrast to scrape chillers, stirring tanks having close-clearance stirrers or cooled crystallization plates, are not fitted with means for reducing the formation of layers of crystals on the heat-transferring surfaces. If, during the operation, a state is reached where the value of the heat transfer resistance owing to the formation of crystal layers is too high, the operation is switched to a second apparatus. While the second apparatus is in use, the first apparatus is regenerated (preferably by melting the crystal layer or by rinsing the apparatus with unsaturated solution). When the heat transfer resistance in the second apparatus reaches a level which is too high, operation is switched back to the first apparatus, etc. This variant can also be carried out by alternating operation between more than two apparatuses. Furthermore, the crystallization can be carried out by conventional evaporation of the solution under reduced pressure.

The mother liquor and the crystallized phthalide can be separated by all known processes of solid-liquid separation. In a preferred embodiment of the invention, the crystals are separated from the mother liquor by filtration and/or centrifugation. The suspension is advantageously pre-thickened using, for example, a hydrocyclone or hydrocyclones, prior to the filtration or centrifugation. Suitable for the centrifugation are all known centrifuges which operate batchwise or continuously. Most advantageously, push-type centrifuges are used, which can be operated in a one-stage or multi-stage manner. Scroll-conveyor centrifuges or helical-conveyor centrifuges (decanters) are also suitable. Filtration is advantageously carried out using nutsch filters which are operated batchwise or continuously, with or without stirrer, or using band filters. The filtration can generally be carried out under superatmospheric pressure or under reduced pressure.

It is possible to include further process steps to increase the purity of the crystals or the crystal cake during and/or after the solid-liquid separation. In a particularly advantageous embodiment of the invention, the separation of the crystals from the mother liquor is followed by one- or multi-stage washing and/or sweating of the crystals or the crystal cake.

The crystals are suitably washed with an amount of washing liquid from 0 to 500 g of washing liquid/100 g of crystals, preferably from 30 to 200 g of washing liquid/100 g of crystals.

Suitable washing liquids are, for example, a) the solvent, if the crystallization is carried out in a solvent, b) liquid pure product or c) liquid feed.

The washing can be carried out in apparatuses customary for this purpose. Washing batteries, where separation of the mother liquor and the washing is carried out in one apparatus, centrifuges, which may be operated in a one-stage or multi-stage manner, or nutsch filters or band filters are advantageously used. The washing can be carried out in centrifuges or on band filters as a one-stage or multi-stage process. In this case, the washing liquid may pass in counterflow to the crystal cake.

Sweating is a local melting off of impure areas. The amount of sweat is advantageously from 0.1 to 90 g of molten crystals/100 g of crystals prior to sweating, preferably from 5 to 35 g of molten crystals/100 g of crystals. Particular preference is given to carrying out the sweating in centrifuges or on band filters.

It may also be suitable to carry out a combination of washing and sweating in one apparatus.

The purity of the resulting phthalide is preferably from 97 to 99.9% by weight, in particular from 98.5 to 99.5% by weight.

If the crystallization has been carried out without addition of an auxiliary and the anodic coproduct has already been removed, mother liquor and washing solution can be recycled into the electrolytic cell without any further work-up, since they essentially comprise a mixture of phthalide and the corresponding starting material.

This also applies in the case where the crystallization has been carried out with the aid of solvents which are also used in the electrolyte.

If the crude phthalide is crystallized from or washed with a solution which is not a component of the electrolyte, the solvent is distilled off and the distillation residue may subsequently be recycled into the electrolytic cell.

One of the main advantages of this process consists in the fact that the proportion of unwanted byproducts is particularly low and that starting material which has not reacted and which essentially can only be separated off as a component of the mother liquor during the crystallization of the phthalide can be recycled into the electrolyte. This also applies to the coproduct and its starting material, the anodic depolarizer. For this reason, the process is particularly economical.

Experimental Part

The percentages in the experimental part are percentages by weight.

EXAMPLE 1

In an undivided electrolytic cell having an anode lead of graphite and a cathode lead of graphite, graphite ring disks having a surface of 1.4 $dm^2$ are arranged in such a way that ten gaps are formed where electrolysis can occur. Two further graphite disks are in contact with the anode and cathode lead. The principle of the cell is known to the person skilled in the art and described for example in D. Degner et al., AIChE Symposium Series No. 185, Vol. 75, p. 14 ff. In this cell, a solution of 20% of Palatinol® M (dimethyl o-phthalate), 13% of p-tert-butyltoluene and 1.2% of methyltributylammonium methylsulfate, dissolved in methanol, was circulated at 40° C. by means of a pump and reacted continuously. Current input: 6 F based on Palatinol M, current density: 2 A/$dm^2$. In the continuous discharge, phthalide had been formed with a selectivity of 90%.

Subsequently, initially the solvent methanol was distilled off under reduced pressure, and the discharge was then distilled under reduced pressure. After the fraction containing the tert-butylbenzaldehyde dimethyl acetal, phthalide was distilled off. This operation was carried out rapidly to avoid vitrification owing to conducting salt decomposition.

The resulting crude material comprised 82% of phthalide and 7% of Palatinol M. The molar ratio (M) was 0.94:1. Since the acetal of tert-butylbenzaldehyde could not be separated off quantitatively from the phthalide, 4% of this component were also found.

After cooling to 25° C. in a heated glass cylinder fitted with a glass frit at the bottom, 22 to 25% of a liquid phase having a phthalide content of 35% and a Palatinol M content of 24% were separated off.

The resulting phthalide phase had a phthalide content of approximately 95%, this was enriched to 99% by meltina off further liquid components at up to 60° C.

Yield of 99% pure phthalide: about 60%

EXAMPLE 2

Crude phthalide from a similar batchwise electrolysis having a Palatinol M content of 13% and a phthalide content of 79% was introduced in molten form into the glass apparatus of Example 1. After cooling to 25° C., 28% of a liquid phase having a phthalide content of 41% and a Palatinol M content of 36% were obtained (molar ratio (M) 0.90:1).

After melting off at up to 60° C., 53% of a 98% pure product containing a residual amount of 0.2% of Palatinol M remained.

Comparative Example

In the cell described in Example 1, a solution of 20% of Palatinol M (dimethyl phthalate), 12% of tert-butyltoluene and 1.2% of methyltributylammonium methylsulfate was reacted at 50° C. Electric current 5 A.

After 4.4 F/mole of Palatinol M, the phthalide content of the solution was 11.2% by weight, this corresponded to a yield of 81%, more than 90% of Palatinol M had been converted. At this time, the molar ratio (M) was 0.93:1 (GC values). At 4.8 F/mole of Palatinol M, the phthalide concentration had reached its maximum with more than 12.2% by weight, corresponding to a yield of about 90%, the molar ratio (M) had increased to 0.97:1. The molar ratio was subsequently increased further, but the phthalide concentration in the electrolyte decreased: at 5.2 F/mole of Palatinol M, the phthalide content was at 11.1% by weight, at a molar ratio (M) of 0.99:1. Only at this stage can a phthalide quality of >98% purity be obtained by distillation.

Thus, the phthalide yield, plotted in a graph as a function of the reaction time, does not approach a limit as would have been expected, but reaches a maximum at a certain conversion and decreases thereafter. A high efficiency for the entire process can therefore only be obtained if the reaction is interrupted at a certain conversion or the reaction mixture is continuously discharged from the reaction vessel and the starting material is subsequently separated off from the reaction mixture by crystallization.

We claim:
1. A process for preparing phthalides by
   I. reducing phthalic acid or phthalic acid derivatives, where the carboxyl groups may be replaced by units which can be derived from the carboxyl groups by a condensation reaction and where one or more of the hydrogens of the o-phenylene unit may be substituted by inert radicals, at a cathode in an undivided electrolytic cell and dissolved in an electrolyte,
   II. discharging the electrolyte from the electrolytic cell when the reaction has proceeded to the stage where the molar ratio (M), formed by the proportion of said phthalides and the sum of the proportions of said phthalides and phthalic acid or phthalic acid derivatives in the electrolyte, is from 0.8:1 to 0.995:1, and
   III. crystallizing the phthalides from the electrolyte and removing them from the mother liquor, if appropriate after distillative work-up of the electrolyte.
2. The process as claimed in claim 1, wherein the phthalic acid or phthalic acid derivatives in step (I) comprises a compound of formula (I)

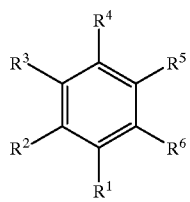

I where the substituents have the following meanings:

$R^1$, $R^2$, $R^3$ and $R^4$: are each, independently of one another, hydrogen, $C_1$- to $C_4$-alkyl or halogen $R^5$, $R^6$:
  a) are each, independently of one another, —COOH or —COOX, where X is $C_1$- to $C_4$-alkyl,
  b) one of the substituents $R^5$ or $R^6$ is —COONY$_4$ and the other substituent is CONH$_2$, where Y is $C_1$- to $C_4$-alkyl or hydrogen,
  c) $R^5$ and $R^6$ together are —CO—O—CO—.

3. The process as claimed in claim 1, wherein step (I) comprises di($C_1$- to $C_3$-alkyl) phthalates.

4. The process as claimed in claim 1, wherein the electrolyte used as solvent comprises an organic solvent or a mixture of water and an organic solvent.

5. The process as claimed in claim 4, wherein the solvent used is methanol.

6. The process as claimed in claim 1, comprising an anodic depolarizer which is methylbenzene or a ring-substituted derivative of methylbenzene in which 1 to 3 hydrogens of the phenyl radical may be replaced by $C_1$- to $C_6$-alkyl radials or $C_1$- to $C_4$-alkoxy radicals.

7. The process as claimed in claim 1, wherein the electrolyte discharged from the electrolysis is worked up distillatively prior to the crystallization.

8. The process as claimed in claim 7, wherein the distillative work-up of the electrolyte is carried out by removing an organic solvent and then a fraction comprising the phthalides distillatively from the electrolyte.

9. The process as claimed in claim 7, where the distillative work-up of the electrolyte is carried out by
   a) removing by distillation in step III essentially only a solvent from the electrolyte
   b) removing by distillation, after step III, two additional fractions from the remaining distillation residue, one of which comprises mainly the phthalides and the other comprises mainly the products which were formed during anodic depolarization.

10. The process as claimed in claim 1, wherein the crystallization of the phthalides is carried out in the absence of auxiliaries.

11. The process as claimed in claim 1, wherein the crystallization of the phthalides is carried out on a cooled surface on which the crystals grow.

12. The process as claimed in claim 1, wherein the mother liquor formed during the crystallization of the phthalide is employed for preparing the electrolyte used in step (I).

* * * * *

UNITED STATES PATENT AND TRADEMARK OFFICE
CERTIFICATE OF CORRECTION

PATENT NO.   : 6,315,884 B1
DATED        : November 13, 2001
INVENTOR(S)  : Pütter et al.

It is certified that error appears in the above-identified patent and that said Letters Patent is hereby corrected as shown below:

<u>Title page,</u>
Item [30], the Foreign Application Priority Data should read:

-- [30]   Foreign Application Priority Data
Sept. 19, 1997   (DE)……………………………..19741423 --

Signed and Sealed this

Second Day of July, 2002

Attest:

JAMES E. ROGAN
Attesting Officer          Director of the United States Patent and Trademark Office